US00PP31051P2

(12) United States Plant Patent
van Swieten

(10) Patent No.: US PP31,051 P2
(45) Date of Patent: Nov. 12, 2019

(54) ***PHALAENOPSIS* ORCHID PLANT NAMED 'PHALGALYI'**

(50) Latin Name: ***Phalaenopsis* hybrid**
Varietal Denomination: PHALGALYI

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,277

(22) Filed: Oct. 25, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

(56) References Cited

PUBLICATIONS

GTITM UPOVROM Citation for 'Phalgalyi' as per QZ PBR 20171106; Apr. 25, 2017; 1 page.*
EU Community Plant Variety Rights Application No. 2017/1106, Application n°A201701197, filed Apr. 24, 2017, 8 pages.
EU Community Plant Variety Office Official Gazette, Mar. 2017, Jun. 15, 2017, cover page and pp. 37, 57.
EU Community Plant Variety Rights Certificate on the Grant, No. EU 50172, issued Sep. 10, 2018, 2 pages.

* cited by examiner

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALGALYI', particularly characterized by having greenish-yellow flowers with yellow lips, 1 to 4 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALGALYI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGALYI'.

The new *Phalaenopsis* plant is a product of a planned breeding program conducted by the inventor in Bleiswijk, The Netherlands. The objective of this breeding program was to create a new *Phalaenopsis* plant with numerous attractive greenish-yellow flowers with yellow lips, suitable for potted plant production.

The new *Phalaenopsis* plant 'PHALGALYI' is a result of cross-pollination made by the inventor in February 2008 in Bleiswijk, The Netherlands, of the proprietary female, or seed parent, *Phalaenopsis* hybrid '11968-04' (unpatented) with the proprietary male, or pollen parent, *Phalaenopsis* hybrid '24245-01' (unpatented).

The new *Phalaenopsis* was selected by the inventor as a single plant within the progeny of the stated cross-pollination in a controlled greenhouse in Bleiswijk, The Netherlands, in April 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGALYI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGALYI' as a new and distinct variety of *Phalaenopsis* plant:

1) Greenish-yellow flowers with yellow lips;
2) 1 to 4 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, bud and foliage of the plant; the colors shown are as true as can be reasonably obtained by conventional photographic procedures. The photographs were taken in a greenhouse in Bleiswijk, The Netherlands, from 50-week old plants in September 2018. Colors in the photographs may differ from the color values cited in the detailed botanical description, which accurately describe the actual colors of the new variety.

DESCRIPTION OF THE NEW VARIETY

Figure 1:
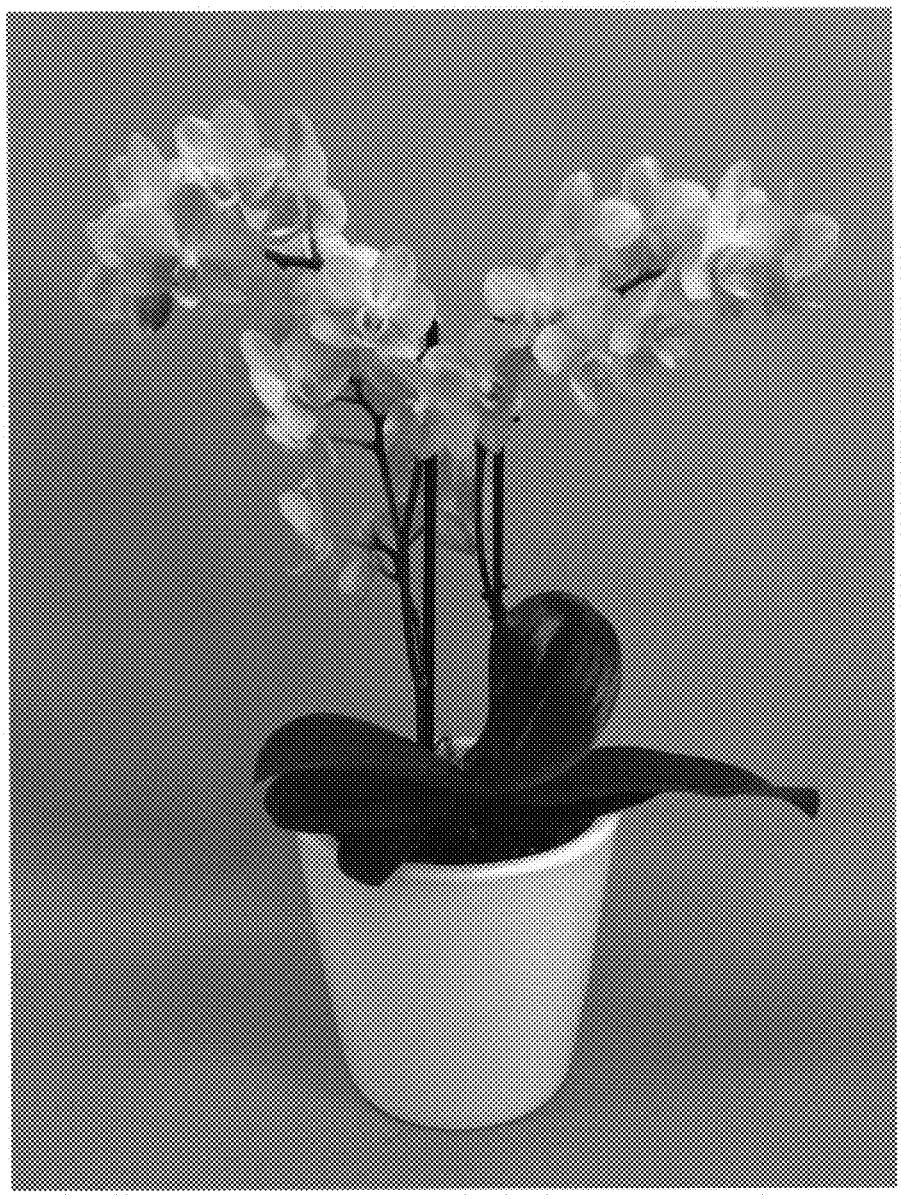
FIG. 1 shows the overall plant habit, including blooms, bud and foliage of 'PHALGALYI'.
Figure 2:
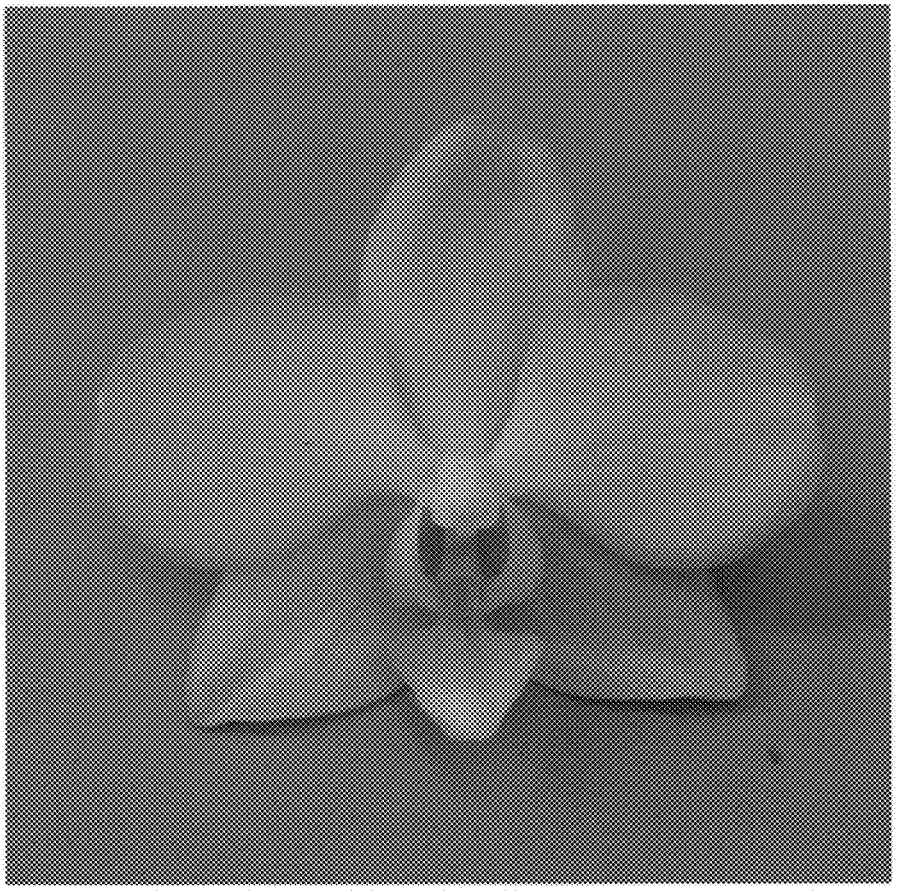
FIG. 2 shows a close-up of a flower of 'PHALGALYI'.
Figure 3:
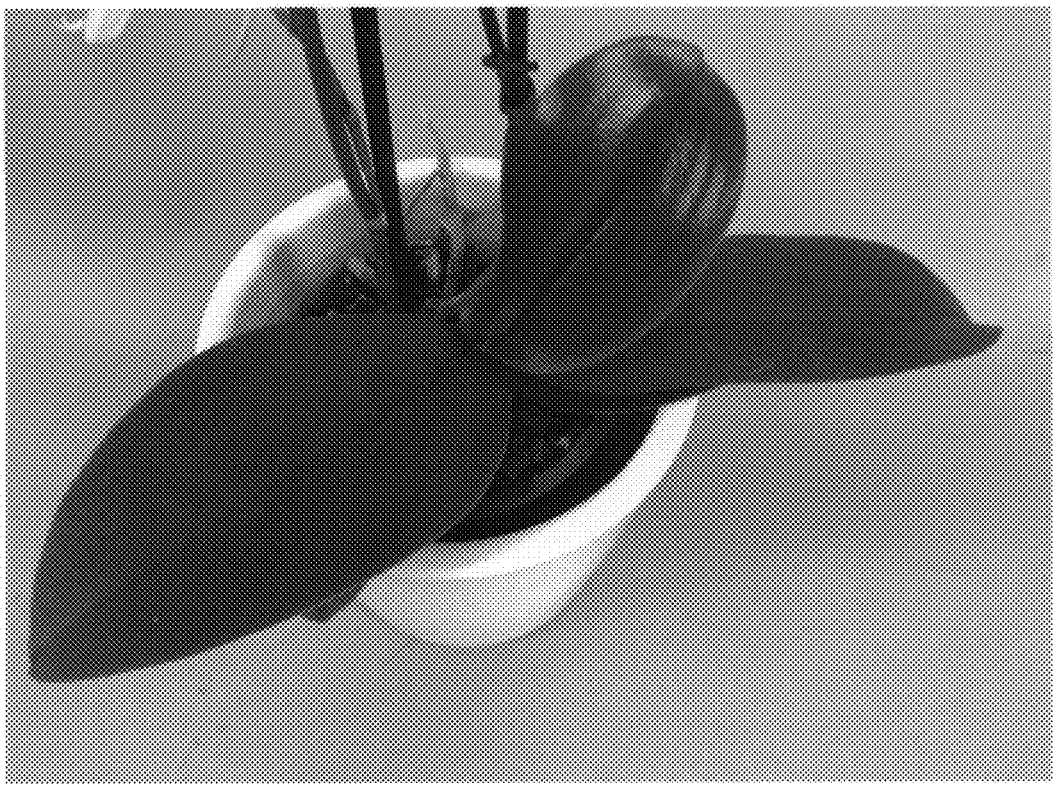
FIG. 3 shows an overhead view of the leaves of 'PHALGALYI'.

The following detailed description sets forth the distinctive characteristics of 'PHALGALYI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in September 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGALYI'.

Parentage:

*Female parent*.—*Phalaenopsis* cultivar '11968-04' (unpatented).

*Male parent*.—*Phalaenopsis* cultivar '24245-01' (unpatented).

Propagation:

*Type*.—Meristem tissue culture.

Roots:

*Root description*.—Greyed-green colored roots (between RHS 190B and 190C) with branching lateral roots having light yellow-green (RHS 145B) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height (from soil level to top of inflorescence)*.—Approximately 32.0 cm to 37.0 cm.

*Width (measured from leaf tips)*.—About 28.0 cm to 30.0 cm.

*Vigor*.—Moderate.

Leaves:

*Mature leaves*.—Quantity per plant: 7 to 9 leaves are produced before flowering. Length (fully expanded): 14.0 cm to 16.0 cm. Width: 6.5 cm to 7.5 cm. Shape: Oblong. Base shape: Moderately elongated. Apex: Acute to obtuse unequal. Leaf blade angle with the petiole (measured from the horizontal position): Between 10 degrees and 20 degrees. Leaf margin: Entire. Color: Upper surface: RHS 146A. Lower surface: RHS 146B. Texture (upper surface): Smooth. Thickness: 2.2 mm to 2.5 mm. Venation: Pattern: Parallel. Color of the midvein: Upper surface: RHS 146A. Lower surface: RHS 146B.

Peduncle:

*Quantity per plant*.—1 to 4.

*Number of flowers per peduncle*.—10 to 19.

*Length*.—32.0 cm to 37.0 cm.

*Diameter*.—3.4 mm to 3.6 mm.

*Strength*.—Strong.

*Aspect*.—Upright to slightly pendant.

*Texture*.—Smooth.

*Color*.—Green (RHS 146B) with a touch of brown (RHS N199A) toward the base.

*Internode length*.—6.0 cm to 7.0 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 140.0 mm to 240.0 mm.

*Flowering time*.—First flowers can be expected 10 to 11 months after planting in a 12 cm (diameter) pot.

*Flower*.—Height: 52.0 mm to 57.0 mm. Diameter: 55.0 mm to 60.0 mm. Depth of lip: 16.0 mm to 18.0 mm.

*Flower longevity*.—On the plant: 10 to 15 weeks.

*Fragrance*.—Absent.

*Flower bud*.—Average size: Length: 18.0 mm to 20.0 mm. Width: 13.0 mm to 15.0 mm. Shape: Egg shaped. Color: Yellow-green (RHS N144D).

*Petals*.—Arrangement: Open/free. Shape: Semi-circular. Apex: Rounded asymmetric. Margin: Slightly undulated. Length (from base to tip): 26.0 mm to 28.0 mm. Width: 24.0 mm to 26.0 mm. Color (when fully opened): Upper surface: Basic color: Yellow-green (RHS 154C to 154D). Over color: Absent. Lower surface: Basic color: Light yellow-green (RHS 154D). Over color: Absent.

*Dorsal sepal*.—Shape: Elliptic. Apex: Rounded symmetric; the tip is slightly folded toward the back. Margin: Entire. Length (from base to tip): 29.0 mm to 31.0 mm. Width: 18.0 mm to 20.0 mm. Color (when fully opened): Upper surface: Basic color: Greenish-yellow (RHS 2B). Over color: Yellow-green (RHS 150B). Lower surface: Basic color: Greenish-yellow (RHS 2B). Over color: Yellow-green (RHS 150A).

*Lateral sepals*.—Shape: Ovate. Apex: Obtuse. Margin: Entire. Length (from base to tip): 29.0 mm to 31.0 mm. Width: 18.0 mm to 20.0 mm. Color (when fully opened): Upper surface: Basic color: Yellow-green (RHS 154B). Over color: Reddish-brown dots (RHS 174A). Lower surface: Basic color: Yellow-green (RHS 150B). Over color: Yellowish-green (RHS N144A) toward the tip.

*Labellum (lip)*.—Whiskers: Present. Length of whiskers: 2.0 mm to 4.0 mm. Color of whiskers: Greenish-yellow (RHS 2B). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 12.0 mm to 14.0 mm. Width: 4.0 mm to 6.0 mm. Color: Yellow (RHS 7A) at the base and one side with reddish-orange (RHS 173A) stripes and spots; white (RHS 155B) on the other side.

*Apical lobe*.—Shape: Ovate. Margin: Entire. Length: 15.0 mm to 17.0 mm. Width: 12.0 mm to 14.0 mm. Color: Yellow (RHS 12A) at the base with very small dots (RHS 173B); white (RHS NN155C) toward whiskers.

*Callus*.—Average size: Small. Height: 3.0 mm to 4.0 mm. Length: 3.0 mm to 4.0 mm. Width: 2.0 mm to 3.0 mm. Color: Yellow (RHS 12A and 13A) dotted (RHS 173B).

Reproductive organs:

*Column*.—Length: 8.0 mm to 10.0 mm. Diameter: 4.5 mm to 4.8 mm. Color: White (RHS NN155C).

*Pollinia*.—Quantity: 2. Diameter: 0.7 mm to 0.9 mm. Color: Orange-yellow (RHS 23A).

*Ovary*.—Length: 8.0 mm to 10.0 mm. Diameter: 1.8 mm to 1.9 mm. Color: Green (RHS 145C).

*Pedicel*.—Length: 25.0 mm to 27.0 mm. Diameter: 1.9 mm to 2.0 mm. Color: Green (RHS 144C).

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGALYI' differs from female parent plant '11968-04' (unpatented) in that 'PHALGALYI' has flowers with a basic color of yellow-green and small calluses, whereas '11968-04' has flowers with a basic color of white and medium calluses.

'PHALGALYI' differs from male parent plant '24245-01' (unpatented) in that 'PHALGALYI' has flowers with an even pattern, whereas '24245-01' has flowers with a dotted/spotted pattern.

'PHALGALYI' is most similar to the commercial *Phalaenopsis* plants named 'PHALCUWIM' (U.S. Plant Pat. No. 26,138) and 'PHALCROBOH' (unpatented). 'PHALGALYI' differs from the commercial variety 'PHALCUWIM' in that 'PHALGALYI' has yellow, dotted calluses, oblong leaves, and ovate apical lobes, whereas 'PHALCUWIM' has orange, spotted calluses, narrow obovate leaves, and elliptic apical lobes.

'PHALGALYI' differs from the commercial variety 'PHALCROBOH' in that 'PHALGALYI' has yellow, dotted calluses and apical lobes that are yellow at the base with very small dots and white toward the whiskers, whereas 'PHALCROBOH' has orange-yellow, dotted calluses and apical lobes that are yellow at the base with yellow-green and white toward the whiskers. Additionally, 'PHALGALYI' has smaller flowers and narrower dorsal sepals than 'PHALCROBOH'.

I claim:

1. A new and distinct variety of *Phalaenopsis* plant named 'PHALGALYI', substantially as described and illustrated herein.

* * * * *